United States Patent [19]

Hatke

[11] 4,143,650

[45] Mar. 13, 1979

[54] DIRECTIONAL DOPPLER ULTRASOUND SYSTEMS FOR BIOSIGNAL ACQUISITION AND METHOD OF USING THE SAME

[75] Inventor: Fred L. Hatke, Skillman, N.J.

[73] Assignee: Hoffmann-La Roche Inc., Nutley, N.J.

[21] Appl. No.: 730,111

[22] Filed: Oct. 6, 1976

[51] Int. Cl.² .............................................. A61B 5/02
[52] U.S. Cl. ................................ 128/2.05 Z; 128/2 V
[58] Field of Search .......................... 128/2.05 Z, 2 V; 73/67.7, 67.8 R, 67.8 S, 618, 620

[56] References Cited

U.S. PATENT DOCUMENTS

| | | | |
|---|---|---|---|
| 3,386,094 | 5/1968 | Kratzer et al. | 343/17.5 |
| 3,386,095 | 5/1968 | Stevens | 343/17.5 |
| 3,388,398 | 6/1968 | Kratzer et al. | 343/17.5 |
| 3,614,785 | 10/1971 | Kratzer | 343/7.7 |
| 3,813,654 | 5/1974 | Clifton et al. | 128/2.05 Z X |
| 3,934,577 | 1/1976 | Romani | 128/2.05 T |
| 3,942,178 | 3/1976 | Hackett | 343/5 PD |
| 3,956,623 | 5/1976 | Clark et al. | 235/186 |
| 3,982,109 | 9/1976 | Klinck et al. | 235/150.3 |
| 3,982,114 | 9/1976 | Hook | 235/181 |
| 3,991,365 | 11/1976 | Takeuchi | 324/78 R |

FOREIGN PATENT DOCUMENTS

2159129 12/1975 Fed. Rep. of Germany ...... 128/2.05 Z

OTHER PUBLICATIONS

Mackay, "Non-Invasive Cardiac Output Measurement" Microvascular Research, vol. 4, pp. 442–443 (1972).
Kalmus "Direction-Sensitive Doppler Device" Proc. IRE, vol. 43, 698–700 Jun. 1955.

*Primary Examiner*—Robert W. Michell
*Assistant Examiner*—Michael H. Thaler
*Attorney, Agent, or Firm*—Jon S. Saxe; George M. Gould; Mark L. Hopkins

[57] ABSTRACT

A directional doppler ultrasound system for biosignal detection and acquisition, particularly for use in fetal monitoring, for example, prior to and during labor and preferably employing a wide beam transducer arrangement, the system enabling operator selection of signals effected by physiologic events having associated therewith motion in given different directions (i.e., the towards and away directions relative to the transducer arrangement). Such a system employs a pair of mixers in which the receive echoes of the transmitted carrier signal are beat with a portion of the carrier signal then being transmitted, wherein the carrier signal input to one of the mixers is phase shifted by 90° relative to the other. The mixer outputs are passed through a constant 90° phase difference network where one input receives a 90° phase shift relative to the other, and both are then coupled to sum and difference amplifiers to provide respective towards and away directional doppler information. In a preferred embodiment the directional system is combined with a doppler ultrasound system employing ranging techniques to provide an overall system having a capability of delivering either or both of a pair of outputs comprising the doppler components of interest in the received echoes which are representative of movement within a selected volume remote from the operative location of the transducer arrangement and selectively associated to the towards and away directions relative to the latter.

20 Claims, 21 Drawing Figures

FIG. 3B ORIGINAL CODE OUTPUT ON LEAD 23a

RANGE SELECTION

FIG. 3C POS. A (4 CM)

FIG. 3D POS. B (8 CM)

FIG. 3E POS. C (12 CM)

FIG. 3F POS. D (16 CM)

FIG. 3G POS. E (20 CM)

FIG. 3H S/H CONTROL SIGNAL ON LEAD 22a

FIG. 7

DIRECTIONAL DOPPLER ULTRASOUND SYSTEMS FOR BIOSIGNAL ACQUISITION AND METHOD OF USING THE SAME

BACKGROUND OF THE INVENTION

This invention relates to directional doppler ultrasound systems for biosignal detection and acquisition. As used herein the term biosignal means a signal produced by or from or derived from a physiological phenomenon, i.e. a biophysical event.

Doppler systems, particularly doppler ultrasound systems, are commonly used to detect biophysical events such as blood flow, heart motion and fetal heart motion. Certain applications (e.g. fetal heart motion) involve detection of a multiplicity of doppler components arising from the desired organ's motion which may then be used to count the rate of occurrence of events or as a time reference for physiologic measurements (e.g. calculating time intervals). Unfortunately, doppler components all too often are present which result from motions of other objects of no interest but which are nevertheless in the field "viewed" by the system. This factor, coupled with the fact that the desired organ (e.g. the heart) may itself contain several moving structures, moving in different directions at different velocities, at the same time as well as in sequence, usually results in the reception of a rather complex composite signal.

In the present art, these complex signals are used directly, and various processing methods such as filtering, resonant circuits, etc. may be used to attempt to reduce the complexity of signals representing a complex event (e.g. a heart beat) to a single pulse. However, in addition to the fact that present doppler arrangements are at times unable to reliably provide from such complex signals the accuracy desired in the medical profession regarding for example interval measurement, there is need to single out certain portions of the signal representing reproducible, predictable, unique physiological events to allow measurement of inter-event details (e.g. in regard to the heart pre-ejection period, left ventricular ejection time, isometric relaxation time, etc.) and there is the need, particularly in monitoring the fetal heart, for singling out single physiologic phenomena to render inter-event counting (e.g. heart rate) more accurate.

Monitoring the heart rate of the fetus is one application of special importance. Here, there is great interest in accurate counting of each beat-to-beat interval (time between heart beats) by doppler ultrasound, and in addition, there is great interest in measuring the time from the fetal ECG to given valve motion in the fetal heart.

More particularly in regard to fetal monitoring per se, it is for example believed by many that short term fetal heart rate (FHR) variability patterns (beat-to-beat changes) may contain information concerning fetal wall being. In addition to their part in forming the long term variability patterns, they may represent the effects of fetal respiratory efforts, the minute adjustments of blood volume in the fetal-placental unit, changes in fetal blood pressure and the effects of drugs. These patterns are of particular interest in antenatal fetal evaluation.

Accurate measurement of RR (R-wave to R-wave) interval variation is known to be easily accomplished after rupture of membranes by the direct (or so-called internal) measurement approach of fetal scalp electrocardiography because the signal for each heartbeat is unique, bold, usually has a high signal-to-noise ratio, is stable and always represents the same physiological event.

In contrast, it is well known that the abdominally (indirectly) derived fetal ECG (i.e. AFECG), though related to a unique physiological event, is not really amenable to beat-to-beat recording because it is frequently obscured by the maternal ECG; its signal-to-noise is often very poor or low and it is unobtainable in over 50% of cases in addition the signal is very difficult to obtain in the critical 32nd to 36th week of gestation. While it has appeal as a potential method of accurate external (to the mother) fetal RR interval measurement, these engineering and physiological considerations prevent the abdominal fetal ECG from realistically approaching true RR interval measurement (as obtained for example through an internal monitoring approach) and therefrom deriving accurate RR interval change or variability.

Moreover, these same considerations prevent the AFECG from realistically approaching the so-called external (ultrasound) doppler in overall ability to obtain a usable record. This is demonstrated for example by the fact that the external doppler system is able to produce heart signals in virtually all patients (fetuses) and is not encumbered by the maternal heart signal, thus rendering its potential for accurate external counting great.

Original research in physiology has demonstrated the cardiac events which compose the complex doppler returns from the fetal heart, and their inter-relationship, and their relation to fetal heart rate. This has led to selection of optimal doppler frequencies and design of patented means for processing (see for example, U.S. Pat. No. 3,763,851 to Hatke et al. and U.S. Pat. No. 3,934,577 to Romani). In the present art the three major doppler components of fetal heart motion, i.e. artrial wall motion, aortic and A-V valve closing, and A-V valve opening, are all presented for counting and listening. These signals include and represent, however, motion of valves, etc. toward and away from the system's transducer arrangement.

As a general consideration, it would be most useful to simplify the doppler signal presented for counting or measurement at the outset by selection of the doppler signal(s) of interest by known physiological characteristics. In the present art, attempts have already been made to simplify the doppler signals for example by use of narrow beam transducers, which allow manual selection of events by careful aiming. This does not eliminate confounding signals in front of or behind the region of interest, or signals from objects moving in the opposite direction.

There exists presently a fetal monitoring system employing ranging techniques which enables substantial elimination of some of the confounding signals such as the doppler signals developed outside, i.e. in front of or behind, the immediate area of interest. It is known, for example, that a ranging-autocorrelation doppler system closely approximates the long-term and to some extent the short term variability obtained by fetal scalp electrocardiography. Such a system is able to provide perhaps a 10db (three-fold) signal enhancement in areas of interest and 30db reduction in other areas. This increases the signal-to-noise ratio and renders accurate counting more feasible.

However, even in the immediate area of interest such as the fetal heart itself, there are a number of movement events occurring naturally for each heart beat (e.g. the atrial motion, AV-valve closings and openings etc.) which give rise to a composite doppler signal which remains complex even with narrow beam transducer operation and ranging techniques, not to mention filtering and other prior art attempts to simplify the composite signal for purposes of, for example, accurate counting.

SUMMARY OF THE INVENTION

It is, therefore, a principle object of this invention to provide a directional doppler system for biosignal acquisition which enables the achievement of distinct discrimination between instances of movement associated with a physiologic event towards the transducer arrangement of the system from those movements away from the transducer arrangement.

It is another principle object of this invention to combine such a directional doppler arrangement with a ranging doppler signal system, i.e. to provide a continuous wave directional doppler system with ranging to derive an even more clear distinct and unique signal as related to a given physiologic event.

It is a further object of this invention to provide an ultrasonic doppler signal system for biosignal acquisition which avoids the necessity for use of narrow beam transducer techniques and the limiting considerations associated therewith.

It is yet another object to provide a doppler ultrasound system for use in the measurement, counting etc. of physiological signals representative of particular biological events, in which facilities are provided for the selection of doppler signals of interest based on directionality as well as facilities for selection of only those signals of interest together with attenuation of signals originating outside the immediate area of interest.

According to the broader aspects of the invention, there is provided, in an ultrasonic directional doppler system for biosignal acquisition, the combination comprising:

(a) ultrasonic transceiver means for transmitting an ultrasonic carrier signal toward a target and receiving signals reflected back therefrom;

(b) mixer means receiving a portion of the carrier signal then being transmitted and said reflected signals for providing a pair of outputs representative of the doppler information contained in said reflected signals, one of said mixer outputs having associated therewith a net phase shift of predetermined amount relative to the other mixer output;

(c) first means connected to said mixer means and receiving the outputs thereof for effecting in one of said mixer outputs a phase shift of predetermined amount with respect to the other; and (d) second means connected to said first means for providing an output representative of the doppler signals contained in said reflected signals associated to target movement in a given direction relative to the point of transmission of the carrier signal.

In a preferred embodiment, the invention in particular concerns improvements in ranging-autocorrelation doppler systems which allow electronic selection of a doppler component (velocity event) moving either toward or away from the transducer (directional doppler). This combination is able to particularly provide electronic selection of doppler events representing motion within a precise volume in a given direction relative to the operative plane of the transducer arrangement. This combination greatly enhances the selectivity of the system and provides a more accurate reference point for counting or measuring.

In this embodiment, the continuous wave doppler ultrasound signal is treated to: (1) enhance the area of interest, i.e. the area where, for example the fetal heart is in the mother's body; (2) reduce signals from other moving organs; and (3) select either signals moving toward or away from the transducer or both combined. As a result of the enhanced selectivity provided thereby, there is derived substantially more accurate measurement of for example beat-to-beat interval because a single event is enhanced.

BRIEF DESCRIPTION OF THE DRAWINGS

The above-mentioned and other objects of this invention will become more apparent by reference to the following description taken in conjunction with the accompanying drawings, in which.

DETAILED DESCRIPTION OF THE INVENTION

The invention represents an outgrowth of efforts undertaken inter alia to find alternatives in improvements to ranging techniques in doppler ultrasound systems which would provide results at least comparable therewith and hopefully superior results. In particular, investigation was undertaken to determine whether the ranged autocorrelated fetal heart doppler signal could be further processed to obtain a unique clear-cut signal representing one point in each heart beat, thus allowing more accurate external (indirect) fetal heart rate (FHR) monitoring.

It is deemed most desirable, for example, to have the system retain "wide beam" capability to allow for the incessant small antenatal fetal motions and to render it more practical for labor. Advantages of wide beam capability are amply demonstrated by considering that with narrow beam transducer operation there is required almost constant attention to signals as for example observed audibly or by viewing an oscilloscope and frequent transducer manipulation (due to the fetal movements) to maintain a unique signal, which thus may be said to provide a somewhat impractical approach. It can be said that these conditions render narrow beam transducer operation useful generally to skilled technicians in a controlled laboratory environment only.

This investigation undertaken revealed generally that processing the doppler for only those signals originating from cardiac structures moving toward or away from the transducer arrangement (i.e. directional doppler) did clarify the signal. The ranging system, by itself, produces a signal which all too often still contains multiple variable components per heart beat, and some background clutter.

Now, while compensations for the inherent doppler variability can usually be adequately provided by for example three-beat averaging techniques, this investigation revealed in particular that the additional capability in such a system (i.e. a ranging-autocorrelation system with three-beat averaging) of selecting a directional component of the doppler enabled the signal to be substantially further clarified, to the point, in fact, where the signal is rendered sufficiently unique enough to more closely approach "internal" beat-to-beat accuracy. It has thus been shown that the electronic selection of the directional signal, based for example on operator auscultation, does permit retention of the wide beam concept and provide a practical arrangement of external beat-to-beat recording.

Figure 1:
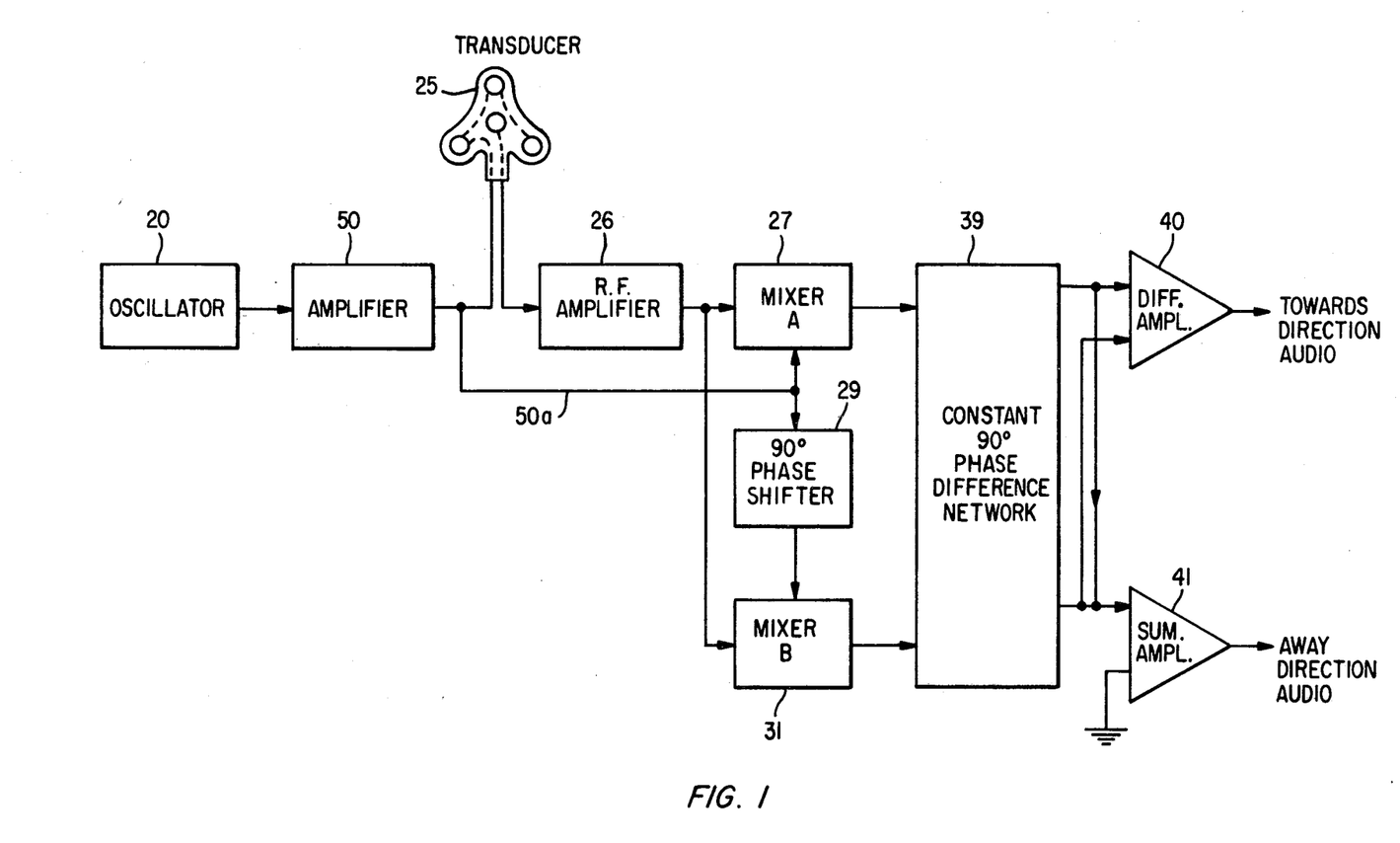
FIG. 1 is a block diagram illustrating an ultrasonic doppler motion detector arrangement employing directional doppler detection according to the invention.

In accordance with the invention, there is illustrated in FIG. 1 an ultrasonic doppler motion detector arrangement with directional doppler detection. In FIG. 1, a transmit signal $$E_t = E_o \cos \omega_o t, \quad (1)$$

where $\omega_o$ is the angular frequency of the transmitted signal in radians per second,
(2MHz in the example embodiment herein depicted) is generated from oscillator 20 and fed through amplifier 50 to an ultrasonic transducer arrangement 25 for transmission to the object under observation. The transducer arrangement 25 may, for example, take the form of the so-called cloverleaf transducer described in U.S. Pat. No. 3,847,016.

The returning signal (echo) including doppler information components $$E_r = k_1 E_o \cos [(\omega_o \pm \omega_d)t + \phi], \quad (2)$$

where $\omega_d$ is the doppler angular frequency shift caused by target motion relative to the transmit transducer and $\phi$ is a constant phase shift representing the transmit time of the signal from transmit to receive transducers,
is picked up by the receive crystals of the transducer arrangement and amplified by amplifier 26. The signal is then fed to a first mixer 27 (i.e. mixer A) and also to a second mixer 31 (i.e. mixer B). In mixers A and B, the receive signal (2) is beat with the transmit signal (1) as provided on line 50a. The transmit signal is, however, processed through a 90° phase shifter 29 prior to being input to mixer B, and in mixer B received signal is thus beat with $$E_t = E_o \cos (\omega_o t - \pi/2). \quad (3)$$

The output of mixer A, where the received or echo signal (2) is beat with the transmit signal (1), may be represented by $$E_A = k_2 E_o \cos (\pm \omega_d t + \phi). \quad (4)$$

Similarly, output of mixer B, where the received or echo signal (2) is phase shifted 90°, i.e. (3), may be represented by the formula $$E_B = k_2 E_o \cos [\pm(\omega_d t + \phi) - \pi/2]. \quad (5)$$

The respective audio outputs, i.e. (4) and (5), from mixers 27 and 31 are both fed to a constant 90° phase difference network 39. Network 39 constitutes an arrangement for providing a 90° phase shift to one of the inputs, for example the mixer A output, relative to the other (mixer B output), regardless of what the particular relative phases of these two signals are when they are input to network 39.

The two outputs of network 39 are each fed to a difference amplifier 40 and a summing amplifier 41, where the difference amplifier 40 provides an output representative of the "towards direction" audio or doppler and the sum amplifier 40 provides an output representative of the "away direction" audio or doppler.

By way of example, with a target approaching (i.e. $+\omega_d$), formulas (4) and (5) become respectively $$E_A = k_2 E_o \cos (\omega_d t + \phi)$$

and $$E_B = k_2 \cos (\omega_d t + \phi - \pi/2).$$

Now, if the "B" signal is delayed 90° relative to "A" by network 39, wherein $E_B$ would now be $$E_B = k_2 E_o \cos (\omega_d t + \phi - \pi),$$

then the summing amplifier 41 output (i.e. $E_A + E_B$) would be zero, whereas there would be an output ($E_A - E_B$) provided by the difference amplifier 40.

On the other hand for a target receding (i.e. $-\omega_d$), then $$E_A = k_2 E_o \cos (\omega_d t - \phi)$$

and $$E_B = k_2 E_o \cos (\omega_d t - \phi + \pi/2).$$

In this case, with the "B" signal delay 90° relative to the "A" signal, wherein $E_B$ would now be $$E_B = k_2 E_o \cos (\omega_d t - \phi),$$

then the output of the difference amplifier 40 would be zero, whereas an output would result from the summing amplifier 41.

It is to be understood that a directional doppler system according to the invention may include the following provisions to permit additional system flexibility and versatility. For example, the arrangement depicted in FIG. 1 may include switching or other suitable conventional means associated with the element 50a and 29 so as to enable a switching or reversing of the inputs to the two mixers 27 and 31 associated to the carrier being transmitted. The main effect provided thereby would be to change the output of, for example, the difference amplifier 40 from the towards direction audio to the away direction audio.

Another provision would be the inclusion of suitable means associated with the phase shifter stage 29 enabling a switching or changing of the sign of the phase shift being applied to the carrier portion input thereto, so as to enable the choice of whether the phase shifted carrier portion leads or lags the other carrier portion input to the mixers by the predetermined amount (±90°).

Additionally, provision may be made in a system according to the invention to switch or reverse the inputs to stage 39. In each case with the above provisions, the main effect would be to change the output of the difference amplifier 40 from the towards to the away direction doppler resultant signal (likewise for the summing amplifier 41, from the away to the towards directional doppler). As will doubtlessly be apparent from this disclosure, other provisions may be made without departing from the spirit or scope of this invention.

Figure 2:
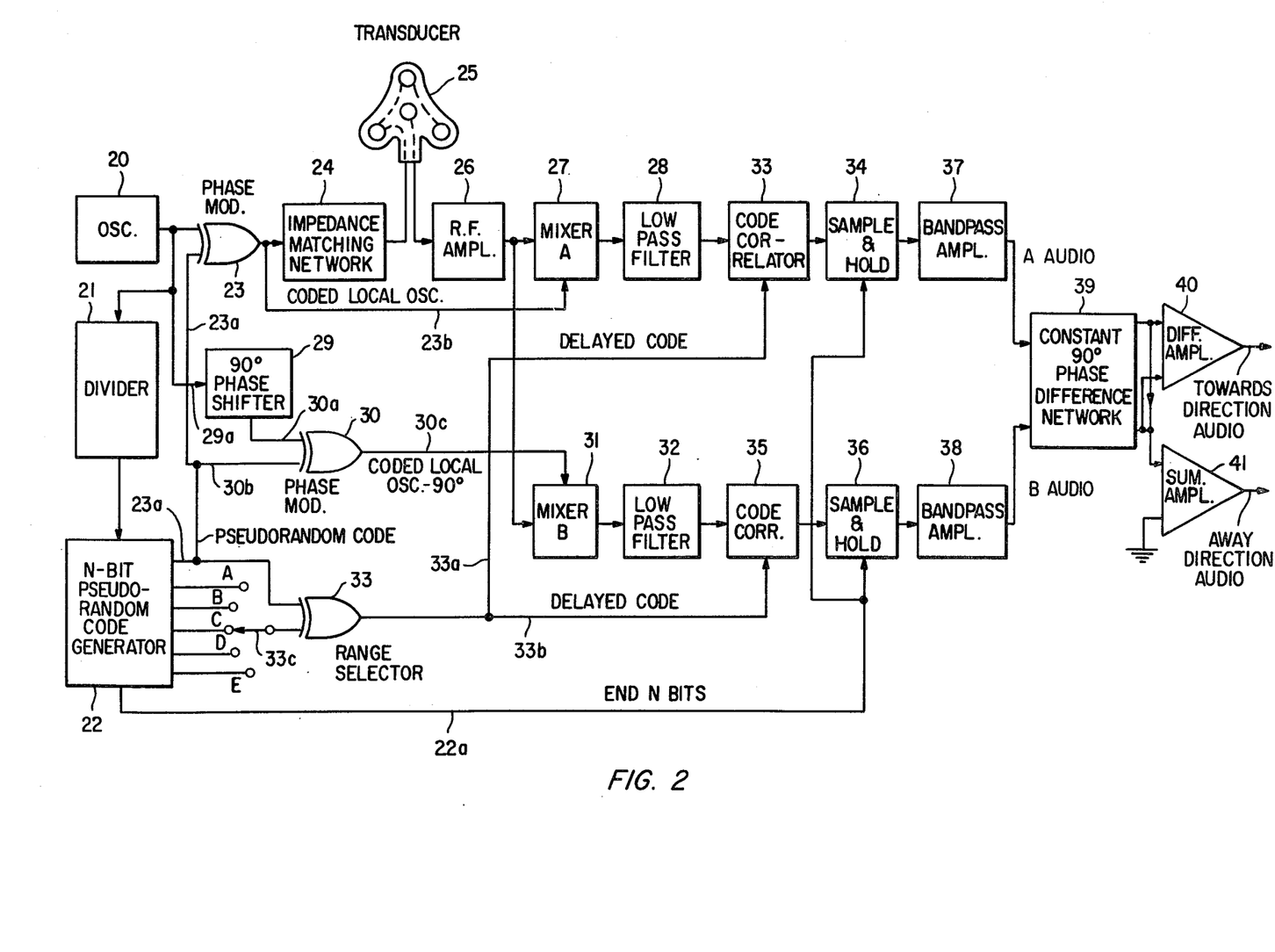
FIG. 2 is a schematic block diagram of an ultrasonic doppler motion detector arrangement employing both ranging and directional doppler detection in accordance with the invention.

Turning to FIG. 2, illustrated therein essentially is the directional doppler arrangement of FIG. 1 in combination with a doppler motion detector system employing a ranging type arrangement, in accordance with the invention. An example of a doppler motion detection arrangement with ranging is the commercially available Fetasonde® 2102 fetal monitoring system of Roche Medical Electronics Inc. For a more complete understanding of the concepts of doppler ranging systems similar to that discussed herein, the reader is referred to the following U.S. Pat. Nos. 3,386,094; 3,386,095; 3,388,398; and 3,614,785.

In FIG. 2, the signal provided for transmission to the target under observation is generated from an oscillator 20 (again, in this example a 2MHz square wave signal, though in terms of principles of operation may be either a square wave or a sine wave) and is fed on the one hand to a divider device 21 wherein the signal is divided to provide an appropriate input signal to an N-bit pseudo-random code generator 22.

The oscillator 20 output is also fed to a 90° phase shifter 29 via line 29a, and to a phase modulator stage 23. Oscillator 20 and phase shifter 29 may together be thought of as a two-phase, 2MHz oscillator supplying a pair of symmetrical square-wave signals 90° out of phase with one another.

The divider stage 21 may be thought of as a pair of programmable four-bit binary counters where, for the present example, one may be a divide-by-thirteen counter and the other a divide-by-eight counter, the two being cascaded to provide a specified output, which in such example is approximately 19KHz.

The N-bit pseudo-random code generator 22 may for the purposes of the example here depicted take the form of a 15-bit pseudo-random number generator. The same may, for example, be comprised of an 8-bit shift register with logic guaranteeing initial startup, wherein the third and fifth bit are multiplied together in an exclusive OR Gate and supplied to the input of the shift register. The output states of the shift register are sampled, and a sample and hold pulse is generated every fifteenth bit.

Figure 3A:
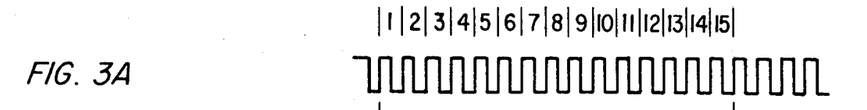
FIGS. 3A-3H graphically illustrate the operations of the pseudo-random code generator of FIG. 2.
Figure 3B:
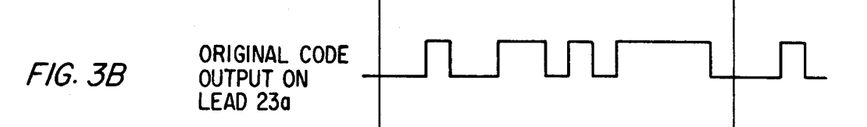
Figure 3C:
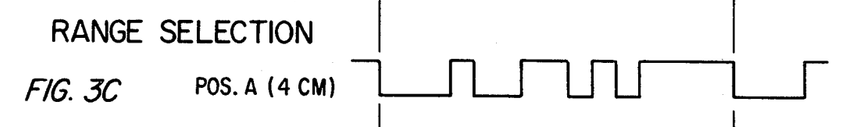
Figure 3D:
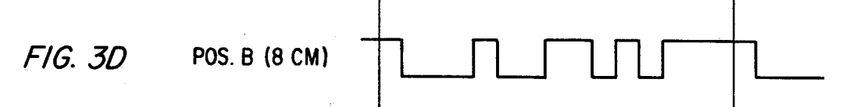
Figure 3E:
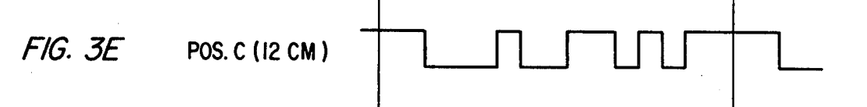
Figure 3F:
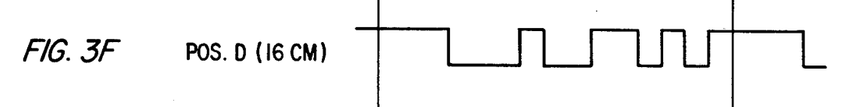
Figure 3G:
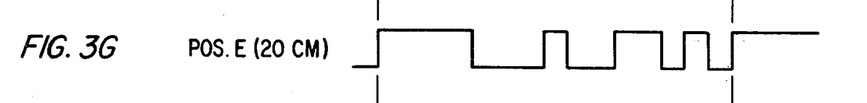

Reference is made to FIGS. 3A-3H illustrating the input and various outputs of the N-bit pseudo-random code generator 22, showing in particular the delayed output code patterns (FIGS. 3C-3G) relative to one another and to the original code output (FIG. 3B). FIG. 3A illustrates the output of divider network 21 which is used to clock the code generator 22.

The initial (original) output (FIG. 3B) of pseudo-random code from generator 22 is fed via line 23a to the phase modulator stage 23, where this code phase modulates the oscillator 20 output, and hence the transmitted signal.

The 15-bit code is also delayed by 1, 2, 3, 4 or 5 clock pulses (FIGS. 3C-3G) according to the range selector 33c position, which provides positions A through E in FIG. 2, corresponding to depth selections of 4cm, 8cm, 12cm, 16cm and 20cm respectively in the example here depicted.

As indicated, the 2 MHz generated signal from oscillator 20 is gated in the transmitter section of FIG. 2 via phase modulator 23 wherein the gating function is the pseudo-random number (waveform FIG. 3B) on line 23a from the generator 22. The phase-coded 2MHz signal output of stage 23 is amplified and fed through a suitably designed impedance matching network 24 and introduced to the transducer arrangement 25 transmit crystals. Phase modulator 23, as shown in FIG. 2, takes the form of an exclusive OR gate. The truth table therefor, illustrating its operation, may be given as follows:

| Code | osc. | Transmit |
|------|------|----------|
| 0    | 0    | 0        |
| 0    | 1    | 1        |
| 1    | 0    | 1        |
| 1    | 1    | 0        | where it may be seen that when the code is 0, the oscillator signal is transmitted as is, whereas when the code is 1, the oscillator signal may be thought of as being transmitted 180° out of phase.

The 15-bit code appearing at output 23a of code generator 22 is also applied to range selector stage 33, which may take the form of an exclusive OR gate. The other input to range selector 33 is the switch arrangement 33c feeding the selected delayed 15-bit code signal. Via stage 33, the selected delayed 15-bit code signal is "multiplied" by the original code so as to generate a delayed code which is then forwarded to the receive side of the system via lines 33a and 33b. At the end (fifteenth bit) of each cycle, pseudo-random code generator 22 outputs the sample and hold pulse (see FIG. 3H) which is also forwarded to the receive side of the system to be utilized thereby as hereinafter discussed.

The oscillator 20 signal output from phase shifter stage 29, as a −90° (in the example depicted) phase-shifted signal, is fed via line 30a to a phase modulator stage 30, which, like phase modulator stage 23, may take the form of an exclusive OR gate. It is to be understood that stage 29 in combination with oscillator 20 may provide a phase shift of +90° relative to the oscillator 20 input to stage 23 as well as any desired phase shift which may be greater or less than 90°. The other input 30b to phase modulator stage 30 constitutes the original code output (FIG. 3B) of generator 22.

As is the case with phase modulator stage 23, the output of phase modulator 30 on line 30c constitutes the phase modulated 2MHz signal coded in accordance with the original code output on line 23a of code generator 22, only delayed 90° in phase relative to the phase modulated signal on line 23b.

The returning (echo) signal from transducer arrangement 25 is coupled to RF amplifier 26 and therefrom to a pair of mixers 27 (mixer A) and 31 (mixer B).

In mixer A, the amplified electrical signal received from the transducer arrangement 25 is beat against the coded oscillator signal input on line 23b supplied from the transmit side of the system. The output of mixer A is passed through a low pass filter 28 where the signal is filtered to remove the 2MHz carrier etc. The output of filter 28 is in turn input to a code correlator stage 33, which also has as an input thereto the delayed code output of stage 33, as provided on line 33a. In code correlator stage 33, the output of filter 28 is multiplied against the delayed code generated by the range depth selector 33c.

Figure 3H:
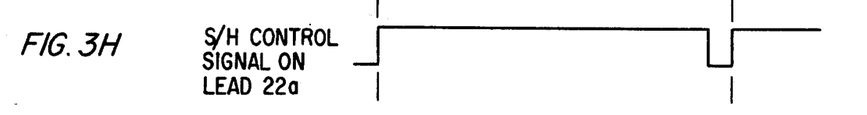

The output of code correlator stage 33 is in turn coupled to a sample and hold stage 34, which has as its second input the sample and hold control signal found on lead 22a as provided by pseudo-random code generator 22 (FIG. 3H). After fifteen bits of possible correlation, the last stored output in code correlator stage 33 is transferred to the sample and hold stage 34, and then the correlation process is begun anew.

The output of sample and hold stage 34 is amplified and filtered in bandpass amplifier stage 37 so as to provde a relative wide band audio signal to the doppler information.

Similarly, the amplified receive signal from RF amplifier 26 is fed to mixer B where it is beat with the 90° phase delayed coded transmit signal output of phase modulator stage 30. In like fashion the output of mixer B is coupled through low pass stage 32 to code correlator stage 35, wherein this input to code correlator 35 is treated, i.e. multiplied, by the delayed code found on input 33b, from range selector 33. Code correlator stage 35 in turn is coupled to sample and hold stage 36 which, like sample and hold stage 34, provides an output under the direction of the sample and hold control signal input from lead 22a. The output of the sample and hold stage 36 in turn is fed to bandpass amplifier 38 to provide also a wideband audio signal of the doppler information. In FIG. 2, the outputs of bandpass amplifiers 37 and 38 are designated the "A" audio and the "B" audio respectively.

These two signals are input to a constant 90° phase difference network 39 which operates in a similar manner to stage 39 of FIG. 1. The two outputs of network 39 are each fed to a difference amplifier 40 and a summing amplifier 41 to provide separate outputs representative of the "towards" direction audio (from difference amplifier 40) and the "away" direction audio (from summing amplifier 41).

In utilizing the directional doppler detection technique together with the ranging type detection, there is required the generation of the 2MHz oscillator output shifted in phase, e.g. by 90°, in reference to the original output utilized in detection. The 90° phase shifted oscillator signal is then phase modulated by the same pseudo-random code prior to being fed to the receive side of the system. In regard to the receive side, the common return signal (echo) is fed to the two separate channels each commencing with a mixer stage, wherein both channels share the same delayed code and sample and hold control signals as generated by (from) the fifteen-bit pseudo-random code generator 22. A key difference between the two channels is the fact that mixer A receives the original phase coded 2MHz oscillator signal whereas mixer B receives this signal shifted (in the example depicted) by 90°.

Figure 4A:
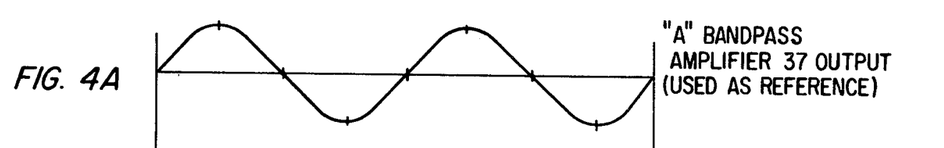
FIGS. 4A-4C graphically illustrate the operation of a portion of the arrangement of FIG. 1.
Figure 4B:
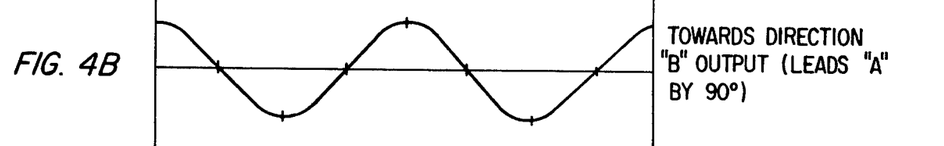
Figure 4C:
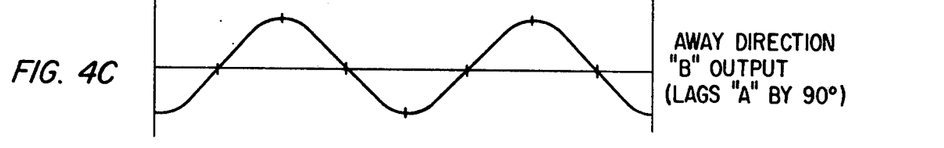

As a result of the 90° phase shift effectively applied to mixer B, the "demodulated" doppler at the "A" bandpass amplifier 37 output and the "B" bandpass amplifier 38 output can be ± 90° phase shifted relative to each other. The phase difference will depend on target motion towards the transducer arrangement 25 (doppler difference frequency increasing in reference to the 2MHz carrier), or target motion away from the transducer arrangement 25 (doppler difference frequency decreasing in reference to the 2MHz carrier). The operation of the arrangement according to FIG. 2 from the bandpass amplifiers 37, 38 is illustrated in FIGS. 4A-4C and FIGS. 5A-5C. FIGS. 4A-4C illustrate respectively: the "A" bandpass amplifier 37 output; "B" bandpass amplifier 38 output where the doppler information content involves a "towards" direction movement, in which the "B" output leads the "A" output by 90°; and the "B" bandpass amplifier 38 output in an "away" direction situation where the "B" output lags the "A" output by 90°.

Figure 5A:
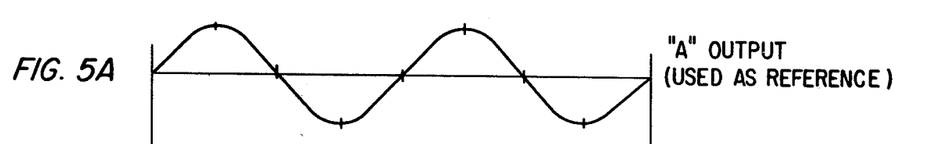
FIGS. 5A-5C graphically illustrate the signal waveforms represented in FIGS. 4A-4C as further operated upon by the arrangement according to FIG. 2.
Figure 5B:
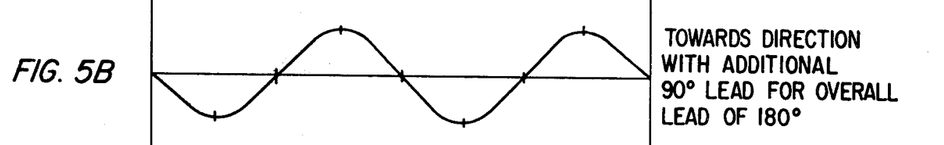
Figure 5C:
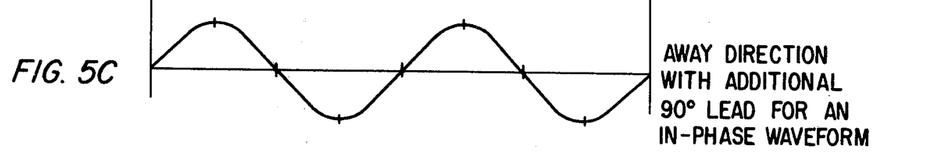

In the arrangement according to FIG. 2 the "A" and "B" bandpass amplifier outputs as hereinbefore indicated, are fed to the constant 90° phase difference filter network 39, wherein the "B" output (which is the A-90° signal in this example) can be shifted another 90° in reference to the "A" audio. This is illustrated in FIGS. 5A-5C. FIG. 5A once again represents the "A" output used as a reference, with FIGS. 5B and 5C representing the "B" output treated by the network 39 in both the "towards" and "away" direction situations. In FIG. 5B, the waveform of FIG. 4B (i.e. the towards direction case) is shown having an additional 90° of lead phase added, thereby resulting in a waveform that is 180° out of phase with the "A" (reference) output. Similarly, in FIG. 5C, the waveform of FIG. 4C (the away direction case) is shown having an additional 90° phase lead, which results in a waveform which is completely in phase with the A (reference) waveform of FIG. 5A.

Thus, with the "A" and "B" signal outputs from the network 39 being fed to the difference 40 and summing 41 amplifiers as indicated in FIG. 2, it may be seen from the waveforms of FIGS. 4A-4C and FIGS. 5A-5C that doppler return in the towards direction, which results in outputs from the network 39 which are 180° out of phase, will give the maximum signal out of the difference amplifier 40 and a cancellation will be effected as to these two waveforms in the summing amplifier 41. Similarly, it may be seen that the doppler return in the away direction, which results in outputs from the network 39 being in phase, will give the minimum signal out of the difference amplifier 40, whereas the addition of the two waveforms in the summing amplifier will achieve a maximum signal therefrom.

By separating the target motion into these two distinct directions, it may be readily seen in connection with FIG. 6, for example, that the doppler return complex is greatly simplified for subsequent signal processing, such as determining the fetal heart rate. In FIG. 6, there is illustrated actual waveforms derived from fetal monitoring, wherein FIG. 6A illustrates the fetal ECG as taken directly from the fetus (e.g. by a suitable scalp electrode inserted through the cervical opening), FIG. 6B illustrates the returning energy of the transmitted ultrasonic signal including doppler components resulting from target (fetal heart) motion and FIGS. 6C and 6D illustrate the towards direction and away direction doppler audio respectively following processing by the directional doppler detection arrangement according to the invention. The waveform of FIG. 6B represents the (external) doppler return indirectly derived through the mother's abdomen via a setup such as is illustrated in FIG. 7. This waveform represents doppler information following treatment by suitable electronic techniques, including ranging, to screen out the maternal heartbeat (as usually derived from the mother's uterine artery or aorta [see FIG. 7]) and any other non-pertinent doppler information such as may have been provided for example by either fetal movement or muscular movements of the mother. As may be seen from FIG. 6B, although only the fetal heartbeat doppler reflections remain, with reduced background, they are variable and complex. By introduction of directional doppler detection in accordance with the invention, it may be seen from FIGS. 6C and 6D that the composite waveform of 6B is able to be readily enhanced as to the various components in the one direction with respect to the other components. This enhancement process related to a particular direction, coupled with reduction to baseline background (the latter of which is also readily apparent in regard to FIGS. 6C and 6D when compared to FIG. 6B) greatly simplifies the doppler information, particularly for counting purposes.

Experiences indicates that with the directional technique alone (i.e. without ranging), the retrieved doppler signal, as in the case of ranging alone, is improved by approximately 10db, and out-of-range motion artifact is effectively 30db down. However, providing directional doppler detection in combination with ranging provides a system which enhances the retrieved doppler signal substantially more. For example, the towards direction relative to the away direction is separable by a factor of 26db or greater, thus demonstrating much improvement in monitoring by indirect means.

There has been described herein in particular a new doppler fetal heart detection system which both enhances the signal of interest and separates the fetal cardiac doppler moving in the "towards" direction from that moving away from the ultrasonic transducer arrangement, the latter for example being a wide beam transducer arrangement. This directional system particularly when employed in combination with a ranging doppler arrangement to form a ranged directional doppler system, provides an output which is, for example, comparable to the fetal scalp ECG in signal-to-noise. It provides a signal which allows external beat-to-beat fetal heart rate monitoring that approaches the accuracy attainable with the fetal scalp ECG, and provides a method deemed simpler for externally measuring fetal cardiac time intervals.

Figure 6A:
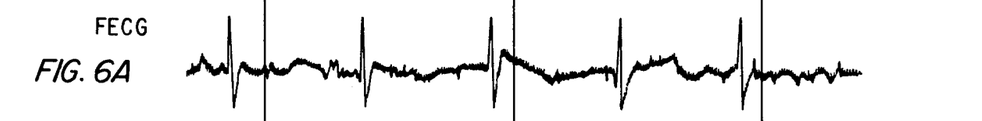
FIGS. 6A-6D are graphic illustrations of respectively direct fetal ECG, the composite processed doppler signal, and the towards and away direction doppler components of the processed composite signal as separated in accordance with the invention.
Figure 6B:
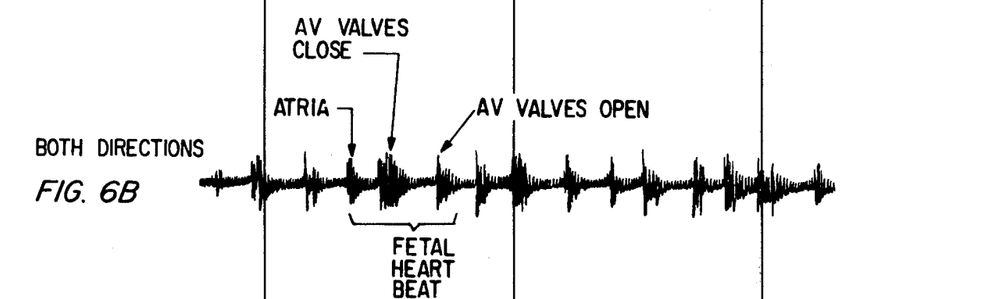
Figure 6C:
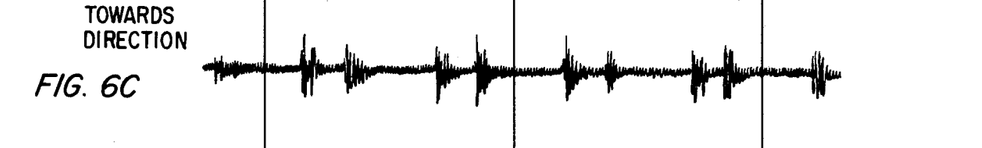
Figure 6D:
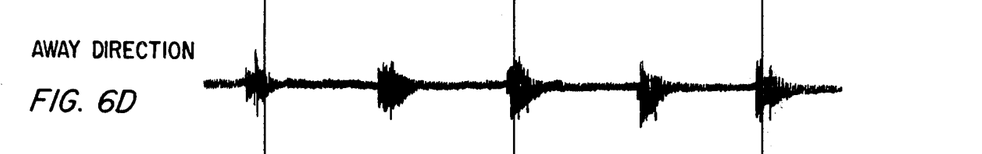
Figure 7:
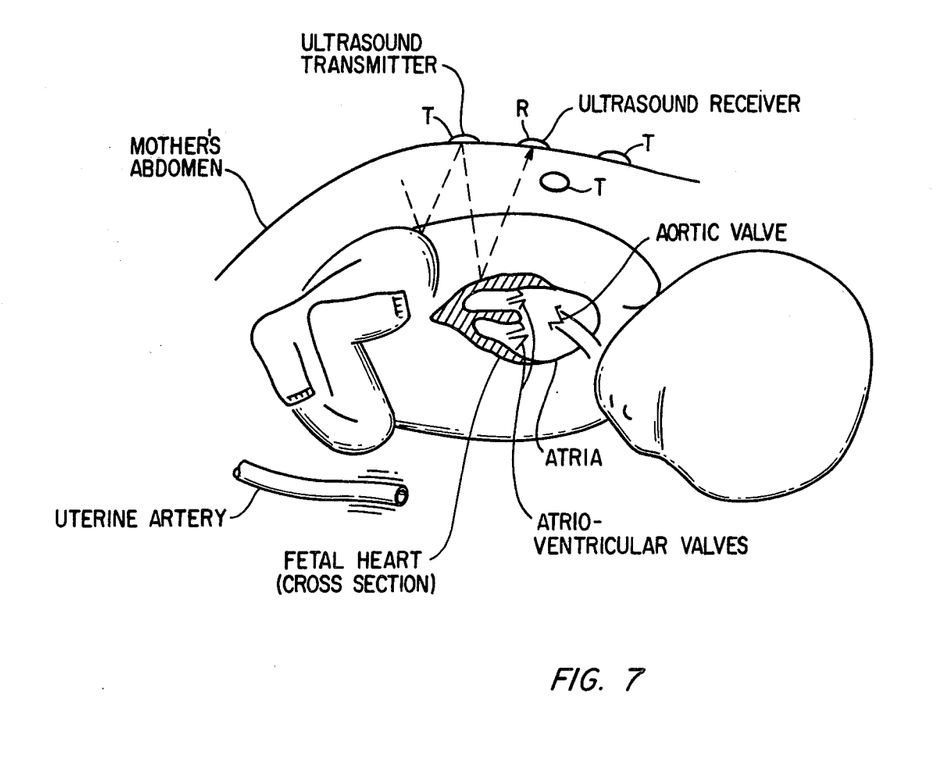
FIG. 7 pictorially illustrates the pregnant maternal abdomen, showing in particular the transducer arrangement placement in relation to the fetal heart.

As is particularly apparent from FIGS. 6B–6D, the directional doppler processing is able to surprisingly clearly separate the cluster of events representing fetal atrial contractions and AV valve closure from the events evidently representing AV valve opening. At least one of the directional signals is usually simple and reproducible, representing a unique point in the cardiac cycle. No significant voltage is lost by this approach and the base line clutter is remarkably reduced, thus providing the potential for accurately counting much weaker signals.

I claim:

1. In an ultrasonic directional doppler system for fetal cardiac monitoring, in particular for distinguishing between movement events of the valves of the fetal heart, in which ultrasonic transceiver means are provided for transmitting an ultrasonic carrier signal toward the fetal heart and receiving signals reflected back therefrom which signals characteristically include multiple components for virtually every fetal heartbeat including those components representative of the fetal valve opening and closing events, the combination comprising:

(a) mixer means, receiving both a portion of the carrier signal being transmitted and said reflected signals, for providing a pair of outputs representative of the doppler information contained in said reflected signals, one of said mixer outputs having associated therewith a net phase shift of predetermined amount relative to the other mixer output;

(b) first means receiving the outputs of said mixer means for effecting in at least one of said mixer outputs a phase shift of predetermined amount with respect to the other; and (c) second means connected to said first means for providing at least one output representative of the doppler signals associated to those components of said fetal heart valve movements in a given direction relative to the point of transmission of the carrier signal, thereby distinguishing at least one unique reproducible event in the fetal cardiac cycle for accurate monitoring of the fetal heart.

2. A system according to claim 1 further including means for selecting whether the output of said second means relates to fetal heart motion in the towards or the away direction relative to the transceiver means.

3. A system according to claim 2 wherein said second means includes means for reversing the inputs to said first means from said mixer means.

4. A system according to claim 2 wherein said mixer means includes a first receive mixer and a second receive mixer each connected to the transceiver means to receive said reflected signals, means for supplying a portion of the carrier signal then being transmitted to said first and second mixers, wherein one of said supplied carrier portions is phase shifted in predetermined amount relative to the other, and means for selecting whether said phase shifted carrier portion supplied to one of said mixers leads or lags by said predetermined amount the carrier portion supplied to the other mixer.

5. A system according to claim 2 wherein said mixer means includes a first receive mixer and a second receive mixer each connected to the transceiver means to receive said reflected signals, means for supplying a portion of the carrier signal then being transmitted to said first and second mixers, wherein one of said supplied portions is phase shifted in predetermined amount relative to the other and means for reversing the respective inputs constituting said carrier signal portions to the first and second mixers.

6. A system according to claim 1 wherein said second means includes third means for providing a plurality of outputs each associated to fetal heart motion in respective different directions.

7. A system according to claim 6 wherein said directions are defined as the away direction and toward direction relative to the transceiver means.

8. A system according to claim 6 wherein the third means comprises summing and difference means coupled to the output of said first means.

9. A system according to claim 1 wherein said second means includes means for providing a summation of the outputs of said first means.

10. A system according to claim 1 wherein said second means includes means for providing the difference of the outputs of said first means.

11. In an ultrasonic directional doppler system for fetal cardiac monitoring, in particular for distinguishing between the opening and closing events of at least one valve of the fetal heart, in which ultrasonic transceiver means are provided for transmitting an ultrasonic carrier signal toward the fetal heart and receiving signals reflected back therefrom, which signals characteristically include multiple components for virtually every fetal heartbeat including those components representative of the fetal valve opening and closing events, the combination comprising:

(a) first and second mixer means connected to said transceiver means for receiving said reflected signals therefrom;

(b) first means for supplying a portion of said carrier signal to be transmitted to said first and second mixer means, said first means including phase shifter means for providing to said second mixer means said carrier signal phase shifted a predetermined amount relative to the carrier signal supplied to said first mixer means;

(c) a constant phase difference network connected to said first and second mixer means for operating on the components of the respective outputs of said first and second mixer means containing doppler signals representative of fetal heart movement to provide relative to one another a phase shift of predetermined amount;

(d) a summing amplifier;

(e) a difference amplifier;

(f) second means for supplying the outputs of said constant phase difference network each to said summing and difference amplifiers to effect at least one output representative of the doppler signals associated to those components of said fetal heart valve movements in a given direction relative to the point of transmission of the carrier signal, thereby distinguishing at least one unique reproducible event in the fetal cardiac cycle for accurate monitoring of the fetal heart.

12. In an ultrasonic doppler correlation system for fetal cardiac monitoring, of the type in which received echoes of a transmitted continuous carrier signal, which has been phase modulated in accordance with a respective preselected code signal, are mixed with the carrier signal then being transmitted, and the mixed output is correlated against said preselected code signal predeterminably delayed to produce an audio signal manifesting a moving target, and in which the extent of delay of said predetermined delayed code signal is selected to provide an amount of correlation which varies directly with the range of the intended moving target, the improvement comprising directional doppler detection means for deriving an output signal which is comprised of the doppler components of the reflected signal which are representative of movement within a selected volume defined by said range remote from and relating to a given direction relative to the point of transmission of the carrier signal.

13. A system according to claim 12 wherein said directional doppler detection means includes means for deriving a pair of output signals each of which is comprised of the doppler components of the reflected signals which are representative of movement within the selected volume and relating to given respective opposite directions relative to the point of transmission of the carrier signal.

14. A system according to claim 13 wherein said directional doppler detection means comprises:

(a) a pair of mixers wherein said received echoes are mixed in a first mixer with said carrier signal and mixed in a second mixer with said carrier signal phase shifted in predetermined amount;

(b) constant phase difference network means connected to said first and second mixers for providing a pair of outputs representative of the respective outputs of said mixers, one of which outputs being phase shifted by said network means in predetermined amount relative to the other; and (c) an amplifier arrangement providing respective summing and difference functions connected to the outputs of said network means for generating respective output signals representative of doppler components of the target's movements in the directions towards and away from the point of transmission of the carrier signal.

15. A system according to claim 14 further including means connected between said mixers and said network means for enabling the mixer outputs to be separately correlated with said code signal delayed said predetermined amount, wherein said network means is adapted to provide a phase shift of predetermined amount between the respective outputs of said correlation means, said amplifier arrangement comprising a summing amplifier and a difference amplifier each having the outputs of said network means both connected thereto for deriving the sum and the difference respectively of said thusly phase shifted outputs of said network means.

16. A continuous carrier directional doppler ultrasound system with ranging for biosignal detection and acquisition, in which there is employed an ultrasonic transceiver arrangement and electronic selection is provided of certain doppler events associated to a given direction relative to the transceiver arrangement occurring within an electronically selected volume remote from the location of said transceiver arrangement, comprising:

(a) code generator means for generating a code signal of predetermined form;

(b) said transceiver arrangement including ultrasonic transmitting means for transmitting a carrier signal modulated by said code and ultrasonic receiving means for receiving the echoes of said transmitted signal as reflected back from a moving target;

(c) mixer means, including first and second mixers respectively supplied with a portion of the modulated carrier signal then being transmitted, one of which mixers having its carrier signal portion predeterminably phase shifted relative to the other, each mixer being connected to said transceiver arrangement to receive said echoes, for providing a pair of outputs representative of the doppler components of said echoes;

(d) code correlation means connected to said mixer means for correlating respectively the mixer means outputs with said code from said code generating means as preselectively delayed in accordance with the desired distance of target search relative to the transceiver arrangement; and (e) means for providing a pair of directional doppler outputs representative of target motion in substantially opposite directions to one another relative to said transceiver arrangement, including constant phase difference network means connected to the respective outputs of said correlation means for effecting a phase shift in one of said outputs of predetermined amount relative to the other, and summing amplifier means and difference amplifier means each connected to both of said outputs of said network means.

17. An ultrasonic directional doppler fetal cardiac monitoring system for extracting at least a first unique repetitive event of the fetal cardiac cycle from the composite doppler ultrasound return signals, comprising first means for obtaining from said return signals doppler signal information representative of motion of at least a portion of a fetal cardiac valve, second means for differentiating between components of said doppler signal information representative of motion of said cardiac valve in at least two directions, and third means for selecting those components associated to one of said directions based upon a pre-established criterion.

18. The system of claim 17 wherein said second means includes means for differentiating between opening and closing events of said fetal cardiac valve.

19. In ultrasonic doppler fetal cardiac monitoring a method for extracting a unique repetitive event of the fetal cardiac cycle from the composite doppler ultrasound return signals, comprising deriving from said return signals doppler signal information representative of motion of at least a portion of a fetal cardiac valve, differentiating between components of said doppler signal information representative of motion of said cardiac valve in at least two directions, and selecting those components associated to one of said directions based upon a pre-established criterion.

20. The method of claim 19 wherein said differentiation step includes differentiating between signal components representative of the opening and closing events of said valve by determining a difference between said events based on motion.

* * * * *